United States Patent [19]
Preissman et al.

[11] Patent Number: 5,833,652
[45] Date of Patent: Nov. 10, 1998

[54] COMPONENT MIXING CATHETER

[75] Inventors: Howard E. Preissman, Los Gatos, Calif.; Y. Pierre Gobin, 10526 Butterfield Rd., Los Angeles, Calif. 90064

[73] Assignee: Y. Pierre Gobin, Los Angeles, Calif.

[21] Appl. No.: 529,935

[22] Filed: Sep. 18, 1995

[51] Int. Cl.⁶ .................................................. A61M 37/00
[52] U.S. Cl. ............................ 604/82; 604/264; 604/280
[58] Field of Search ................................ 604/264, 82, 280

[56] References Cited

U.S. PATENT DOCUMENTS

| | | | |
|---|---|---|---|
| 5,053,004 | 10/1991 | Markel et al. | 604/43 |
| 5,053,023 | 10/1991 | Martin | 604/280 |
| 5,106,368 | 4/1992 | Uldall et al. | 604/43 |
| 5,195,962 | 3/1993 | Martin et al. | 604/43 |
| 5,211,627 | 5/1993 | William | 604/82 |
| 5,346,471 | 9/1994 | Raulerson | 604/43 |
| 5,350,358 | 9/1994 | Martin | 604/43 |
| 5,378,230 | 1/1995 | Mahurkar | 604/43 |
| 5,380,276 | 1/1995 | Miller et al. | 604/28 |
| 5,425,723 | 6/1995 | Wang | 604/264 |

FOREIGN PATENT DOCUMENTS

WO 94/26341  11/1994  WIPO .

*Primary Examiner*—Wynn Wood Coggins
*Assistant Examiner*—N. Kent Gring
*Attorney, Agent, or Firm*—Townsend and Townsend and Crew LLP

[57] ABSTRACT

A component mixing catheter (2) includes a catheter shaft (4) having proximal and distal ends (6, 8) and defining first and second lumens (10, 12). The catheter shaft has an exterior opening (16) at or near its distal end (8) which is fluidly coupled to the first lumen. One or more connecting passages (14) fluidly connect the first and second lumens at a position (30) spaced apart from the exterior opening. The second component passes through the connecting passage and mixes with the first component at a mixing region (25) within the first lumen just prior to exiting the catheter at the exterior opening for maximum therapeutic effect or diagnostic accuracy.

44 Claims, 2 Drawing Sheets

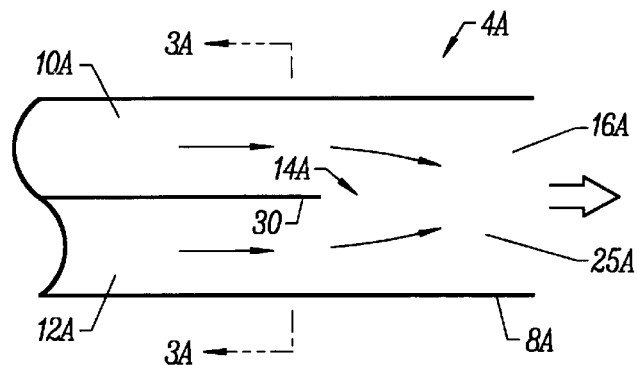
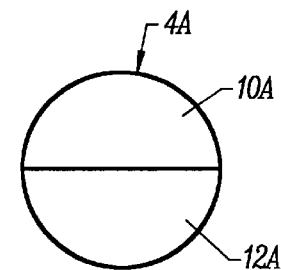
FIG. 3
FIG. 3A
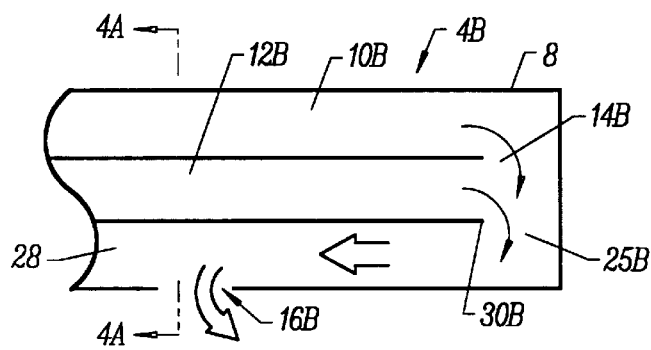
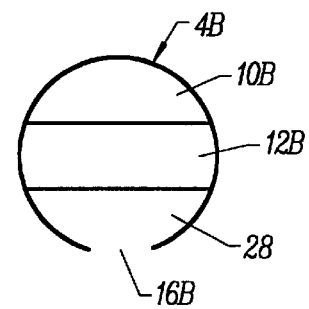
FIG. 4
FIG. 4A
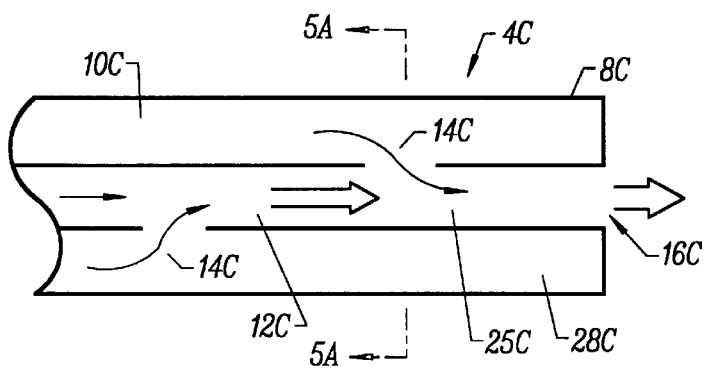
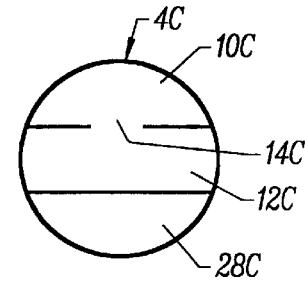
FIG. 5
FIG. 5A 5,833,652

COMPONENT MIXING CATHETER

BACKGROUND OF THE INVENTION

Catheters are used for many different medical reasons. One use is to deliver drugs or other substances to a target site within the body in a region accessible by the tip of a catheter. However, some compounds are not as effective when pre-mixed. For example, they may have a short half life or they may need to be mixed at the target site for other reasons to achieve maximum therapeutic effect or more accurate diagnostic results.

Conventional methods for delivering two components via catheter include the following. One way is to infuse one substance through an outer or guiding catheter and the other through an inner or microcatheter, the distal end of the inner catheter extending out past the distal end of the guiding catheter. Another method is to infuse the two components alternately through the same microcatheter. Finally, two microcatheters could be placed side by side and directed to the target site. All of these solutions have been proven less than totally satisfying.

SUMMARY OF THE INVENTION

The present invention is directed to a catheter and a method for delivering a substance to a target site using the catheter by which two or more components constituting the substance are mixed at the distal end of the catheter just prior to being discharged from an exterior opening at the distal end of the catheter to the target site.

The catheter includes a catheter shaft having proximal and distal ends and define first and second lumens. The catheter shaft has an exterior opening at or near its distal end which is fluidly coupled to the first lumen. One or more connecting passageways fluidly connect the first and second lumens at one or more positions spaced apart from the exterior opening. Therefore, flowing first and second components through the first and second lumens causes the components to combine as the second component passes through the passageway to mix with the first component at a mixing region within the first lumen prior to exiting the catheter at the exterior opening. This way, a substance to be delivered to the target site within a patient is mixed just prior to being applied to the target site for maximum therapeutic effect or diagnostic accuracy.

A primary advantage of the invention is its flexibility. Two or more individual components can be mixed just prior to delivery to the target site through the exterior opening at the distal end of the catheter. The time, amount and turbulence of the mixing can be varied by changing the size and placement of the connecting passages, the distance from the connecting passages to the exterior opening, the placement and shape of the exterior opening, the use of turbulence-inducing elements, and other such techniques. Also, when three or more components are mixed together, mixing can be effected serially or simultaneously, or a combination of the two.

With the present invention, maximum therapeutic effect or diagnostic accuracy can be achieved by mixing the components of the substance being applied to the target area just prior to their application. For example, plasmine can be created using plasminogen and TPA as the first and second components mixed just before delivery of the plasmine to the target site. This minimizes the time between mixing and delivery which is so important for substances, such as plasmine, which have a short half-life. Other components may have a complementary physiologic action. Examples of this include a drug that disrupts the blood brain barrier, such as RMP-7, a chemotherapeutic agent, such as carboplatin, or a two-part epoxy for embolic therapy. In such cases, it is necessary or at least desirable to mix the components only moments before delivery to the target site.

Other features and advantages of the invention will appear from the following description in which the preferred embodiments have been set forth in detail in conjunction with the accompanying drawings.

BRIEF DESCRIPTION OF THE DRAWINGS

FIGS. 3 and 3A are simplified side and end cross-sectional views of an alternative embodiment of the tip of the mixing catheter of FIG. 2;

FIGS. 4 and 4A are views similar to FIGS. 3 and 3A but showing the mixing of first and second components at the distal end of the catheter and exiting the catheter at an external opening spaced apart from the distal end; and FIGS. 5 and 5A are views similar to FIGS. 4 and 4A but show the mixing of three different components and passing the combined substance through an external opening at the distal end of the catheter.

DESCRIPTION OF THE PREFERRED EMBODIMENTS

Figure 1:
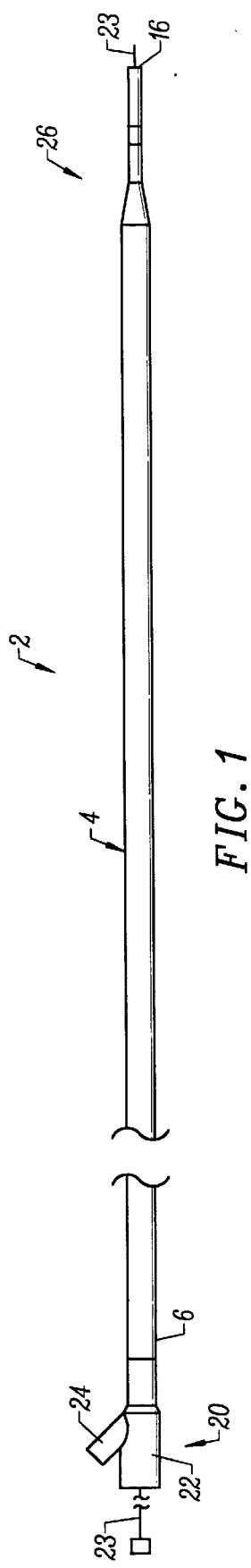
FIG. 1 is an overall view of a mixing catheter made according to the invention.
Figure 2:
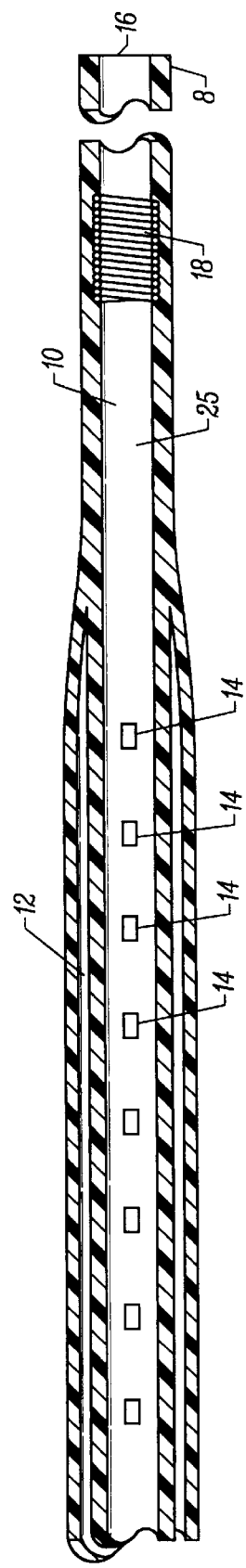
FIG. 2 is an enlarged cross-sectional view of the tip of the catheter of FIG. 1.

FIGS. 1 and 2 illustrate a mixing catheter 2 including a dual lumen catheter shaft 4 having proximal and distal ends 6 and 8 respectively and a length of about 100 to 150 cm (39 to 59 inches), the length, of course, being determined by the patient and the procedure. When mixing catheter 2 is used as a microcatheter for use in procedures such as thrombolysis, chemotherapy or embolic therapy, catheter shaft 4 will have an outside diameter of about 2 to 5 French (0.67 to 1.67 mm).

Catheter shaft 4 is a dual lumen, coaxial catheter shaft including a first, inner lumen 10 and a second, external lumen 12. External lumen 12 terminates about 1–10 cm from distal end 8. Lumens 10, 12 are fluidly coupled through a number of connecting passages 14. This arrangement permits the two components passing through first and second lumens 10, 12 to mix within first lumen 10 prior to exiting an exterior opening 16 formed at distal end 8. A portion of the length of first lumen 10 between connecting passages 14 and external opening 16 is defined by a coil 18. Coil 18 is made of platinum or other radiopaque material and is used to give the tip radiopacity during fluoroscopy.

Proximal end 6 of catheter 4 is connected to a proximal end connector 20 having a main or coaxial arm 22 through which a guidewire 23 can be inserted through first lumen 10 and then, after guidewire 23 has been withdrawn, coupled to a source of liquid or other flowable material. Connector 20 also includes a side arm 24 fluidly coupled to second lumen 12 for the passage of liquid or other flowable material through the second lumen, through connecting passages 14 and into first lumen for mixing in a mixing region 25 of first lumen 10 with the first component.

In use, once the target site is identified, the tip 26 of catheter shaft 4 is directed to the target site using guidewire 23 in a conventional manner. Once properly located at the target site, guidewire 23 can be removed from within first lumen 10 and first and second components can be directed through and second lumens 10, 12 for mixing within mixing region 25 of first lumen 10. Use of mixing catheter 2 permits two different components to be mixed just prior to delivery to the target site through external opening 16 for maximum therapeutic effect in the case of, for example, treatment of thrombosis using plasminogen or TPA or treatment of tumors using RMP-7 or carboplatin.

FIGS. 3 and 3A illustrate an alternative embodiment of the invention in which first and second coaxial lumens 10, 12 are replaced by first and second side-by-side lumens 10A, 12A, both of which terminate at a position spaced apart from external opening 16A at distal end 8A.

FIGS. 4 and 4A illustrate a three-lumen catheter 4B including first and second lumens 10B, 12B and a third lumen 28. Liquid or other flowable material is pumped through lumens 10B, 12B which terminate at a position 30B adjacent distal end 8. However, exterior opening 16B is formed through an external wall defining third lumen 28 spaced apart proximally from position 30B. As in the embodiments of Figs. 2 and 3, the first and second components both have an opportunity to mix within mixing region 25B just prior to exiting catheter 4B through external opening 16B.

FIGS. 5 and 5A illustrate a three-lumen catheter 4C similar to catheter 4B of FIG. 4 but adapted to have three different components pumped through lumens 10C, 12C and 28C. External opening 16C is at distal end 8 while passages 14C coupling first and second lumens 10C, 12C is spaced apart proximally from distal end 8 and passages 14C coupling second and third lumens 12C, 28C is spaced apart proximally from the passages 14C coupling first and second lumens 10C, 12C. This permits the sequential mixing of three different components by the staggered placement of connecting passages 14C. If desired, other sizing and positioning of connecting passages 14C could be used according to the mixing sequence and amounts desired.

Modification and variation can be made to the disclosed embodiments without departing from the subject of the invention as defined in the following claims. For example, more than one exterior opening 16 can be used. Turbulence-inducing structure can be used in mixing region 25.

What is claimed is:

1. A catheter comprising:
    a catheter shaft having proximal and distal ends and first and second coaxial lumens, wherein the first lumen has an exterior opening at or near the distal end of the shaft and said lumens are isolated from each other by a lumenal wall therebetween, said lumenal wall having at least one passage therein near the distal end of the catheter to permit flow between the lumens; and a connector on the proximal end of the catheter shaft, said connector having one arm connected to the first lumen and a second arm connected to the second lumen, whereby components may be separately introduced through the two arms and mix only when one component flows from the second lumen through the passage into the first lumen.

2. The catheter according to claim 1 further comprising an exterior opening wherein the exterior opening in the catheter shaft is located at the distal end of the shaft.

3. The catheter according to claim 1 wherein the second lumen terminates at a position spaced apart from the distal end of the shaft.

4. The catheter according to claim 1 wherein the passage includes a plurality of openings fluidly coupling the first and second lumens.

5. The catheter according to claim 1 wherein the catheter shaft comprises a third lumen fluidly coupled to the first and second lumens.

6. The catheter according to claim 5 further comprising a passage connecting the first and second lumens to one another at a position spaced apart from the opening by a chosen distance, a second passage connecting the first and third lumens at a second position spaced apart from the opening by a second chosen distance.

7. The catheter according to claim 6 wherein said chosen distance and said second chosen distance are different distances.

8. A method for delivering a substance to a target site comprising the following steps:
    flowing first and second components through first and second coaxial lumens of a catheter to a distal portion of said catheter;
    combining said first and second components within said distal portion of the catheter to form said substance; and
    delivering said substance to the target site from the distal portion of the catheter.

9. The method according to claim 8 further comprising the steps of:
    guiding the distal portion of the catheter to the target site using a guidewire; and
    removing the guidewire from the catheter.

10. The method according to claim 8 wherein the delivering step is carried out by delivering said substance through an opening formed at the distal end of the catheter.

11. The method according to claim 8 wherein said combining step is carried out within the first lumen.

12. The method according to claim 8 wherein the combining step is carried out by flowing the second component through a plurality of openings into the first lumen.

13. The method according to claim 8 wherein the combining step is carried out using plasminogen and TPA as the first and second components to create plasmine as the substance.

14. The method according to claim 8 wherein the combining step is carried out using first and second chemically incompatible materials as said first and second components.

15. The method according to claim 14 wherein the combining step is carried out with the first material being a blood brain barrier disrupter and the second material being an anticancerous agent.

16. The method according to claim 8 wherein the combining step is carried out using liquid first and second components.

17. A catheter comprising:
    a catheter shaft having proximal and distal ends and defining first, second, and third lumens, said catheter shaft having an exterior opening, fluidly coupled to the first lumen, at or near the distal end of the shaft;
    a passage connecting the first and second lumens to one another at a position spaced apart from the opening by a first chosen distance; and
    a second passage connecting the first and third lumens at a second position spaced apart from the opening by a second chosen distance.

18. The catheter according to claim 17 wherein said first chosen distance and said second chosen distance are different distances.

19. A method for delivering a substance to a target site comprising the following steps:
    flowing first and second components through first and second lumens of a catheter to a distal portion of said catheter;

combining said first and second components within said distal portion of the catheter by flowing the second component through a plurality of openings into the first lumen to form said substance; and delivering said substance to the target site from the distal portion of the catheter.

20. A method for delivering a substance to a target site comprising the following steps:

flowing first and second liquid components through first and second lumens of a catheter to a distal portion of said catheter;

combining said first and second liquid components within said distal portion of the catheter to form said substance; and delivering said substance to the target site from the distal portion of the catheter.

21. The method according to claim 20 further comprising the steps of:

guiding the distal portion of the catheter to the target site using a guidewire; and removing the guidewire from the catheter.

22. The method according to claim 20 wherein said combining step is carried out within the first lumen.

23. The method according to claim 20 wherein the combining step is carried out by flowing the second component through a plurality of openings into the first lumen.

24. The method according to claim 20 wherein the combining step is carried out using plasminogen and TPA as the first and second components to create plasmine as the substance.

25. The method according to claim 20 wherein the combining step is carried out using first and second chemically incompatible materials as said first and second components.

26. The method according to claim 25 wherein the combining step is carried out with the first material being a blood brain barrier disrupter and the second material being an anticancerous agent.

27. A system for mixing components comprising:

a catheter having a shaft;

the catheter shaft having proximal and distal ends and defining a first lumen and a second lumen;

the catheter shaft having an exterior opening, fluidly coupled to the first lumen, at or near the distal end of the shaft;

a passage connecting the first and second lumens to one another at a position spaced apart from the opening by a chosen distance; and a first liquid source fluidly connected to said first lumen; and a second liquid source fluidly connected to said second lumen.

28. The system according to claim 27 wherein the first and second lumens are located side-by-side.

29. The system according to claim 27 wherein the second lumen terminates at a position spaced apart from the distal end of the shaft.

30. A system for mixing components comprising:

a catheter having a shaft;

the catheter shaft having proximal and distal ends and defining a first lumen and a second lumen;

the catheter shaft having an exterior opening, fluidly coupled to the first lumen, at or near the distal end of the shaft;

a passage connecting the first and second lumens to one another at a position spaced apart from the opening by a chosen distance;

a first liquid source fluidly connected to said first lumen; and a second liquid source fluidly connected to said second lumen;

wherein the catheter shaft comprises a third lumen fluidly connected to at least one of said lumens.

31. The system according to claim 30 wherein the first and second lumens are located side-by-side.

32. The system according to claim 30 wherein the second lumen terminates at a position spaced apart from the distal end of the shaft.

33. The catheter according to claim 30 further comprising a second passage connecting the first and third lumens at a second position spaced apart from the opening by a second chosen distance.

34. The catheter according to claim 33 wherein said chosen distance and said second chosen distance are different distances.

35. A catheter comprising:

a catheter shaft having proximal and distal ends and defining first and second coaxial lumens, wherein the second lumen terminates at a position spaced apart from the distal end of the shaft;

the catheter shaft having an exterior opening, fluidly coupled to the first lumen, at or near the distal end of the shaft;

a passage connecting the first and second lumens to one another at a position spaced apart from the opening by a chosen distance.

36. The catheter according to claim 35 wherein the exterior opening in the catheter shaft is located at the distal end of the shaft.

37. The catheter according to claim 35 wherein the passage includes a plurality of openings fluidly coupling the first and second lumens.

38. The system according to claim 35 wherein the second lumen terminates at a position spaced apart from the distal end of the shaft.

39. A catheter comprising:

a catheter shaft having proximal and distal ends and defining a first coaxial lumen, a second coaxial lumen, and a third lumen fluidly coupled to the first and second lumens;

the catheter shaft having an exterior opening, fluidly coupled to the first lumen, at or near the distal end of the shaft and;

a passage connecting the first and second lumens to one another at a position spaced apart from the opening by a chosen distance.

40. The catheter according to claim 39 wherein the exterior opening in the catheter shaft is located at the distal end of the shaft.

41. The catheter according to claim 39 wherein the passage includes a plurality of openings fluidly coupling the first and second lumens.

42. The catheter according to claim 39 further comprising a second passage connecting the first and third lumens at a second position spaced apart from the opening by a second chosen distance.

43. The catheter according to claim 42 wherein said chosen distance and said second chosen distance are different distances.

44. The system according to claim 39 wherein the second lumen terminates at a position spaced apart from the distal end of the shaft.

* * * * *